(12) United States Patent
Vunjak-Novakovic et al.

(10) Patent No.: US 9,206,383 B2
(45) Date of Patent: Dec. 8, 2015

(54) BIOREACTOR, DEVICES, SYSTEMS AND METHODS

(75) Inventors: Gordana Vunjak-Novakovic, New York, NY (US); Warren Grayson, New York, NY (US); Qun Wan, New York, NY (US); Donald O. Freytes, Nutley, NJ (US); Amandine Godier-Furnémont, Franklin Lakes, NJ (US); Nina Tandon, New York, NY (US); Keith Yeager, Jersey City, NJ (US); George Eng, New York, NY (US); Sarindr Bhumiratana, Woodside, NY (US); Robert Maidhof, North Valley Stream, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 508 days.

(21) Appl. No.: 12/961,309

(22) Filed: Dec. 6, 2010

(65) Prior Publication Data

US 2011/0136225 A1     Jun. 9, 2011

Related U.S. Application Data

(60) Provisional application No. 61/267,405, filed on Dec. 7, 2009.

(51) Int. Cl.
*C12N 5/071* (2010.01)
*C12M 1/34* (2006.01)
(Continued)

(52) U.S. Cl.
CPC ............... *C12M 23/44* (2013.01); *C12M 41/48* (2013.01)

(58) Field of Classification Search
CPC ...... C12M 41/48; C12M 23/44; C12M 21/08; C12M 25/14; C12M 27/14; C12M 29/10; C12M 35/04; G06T 7/0012; G06T 2207/30024
USPC .......................... 435/325, 288.7, 289.1, 286.1
See application file for complete search history.

(56) References Cited

U.S. PATENT DOCUMENTS 7,635,586 B2 * 12/2009 West .......................... 435/286.1
8,216,831 B2    7/2012 Kobayashi et al.
(Continued)

OTHER PUBLICATIONS

Alvarez-Barreto, J.F., et al., "Flow Perfusion Improves Seeding of Tissue Engineering Scaffolds with Different Architectures", Ann Biomed Eng, 2007, 35(3), p. 429-442.
(Continued)

*Primary Examiner* — William H Beisner
*Assistant Examiner* — Danielle Henkel
(74) *Attorney, Agent, or Firm* — Miles & Stockbridge P.C.; Mark A. Catan

(57) ABSTRACT

Disclosed are bioreactor devices, systems and methods. A bioreactor system can include one or more bioreactor modules that can be individually controllable and identifiable. A bioreactor module can be connected to one or more functional modules such as a pump module, a stimulation signal generation module, a motor module, a mechanical transmission module, a gas exchange module, a temperature module, a humidity module and/or a $CO_2$ module, among others. The bioreactor and functional modules can include standard or universal connectors to facilitate connection and movement of modules. The bioreactor system can be controlled and/or monitored by a controller that can individually identify and control each connected module and that can be adapted to collect signal data from sensors embedded in any of the modules.

20 Claims, 8 Drawing Sheets

(51) Int. Cl.
C12M 3/00 (2006.01)
C12M 1/36 (2006.01)

(56) References Cited

U.S. PATENT DOCUMENTS

| | | | |
|---|---|---|---|
| 8,383,397 B2* | 2/2013 | Wojciechowski et al. | 435/289.1 |
| 8,492,140 B2* | 7/2013 | Smith et al. | 435/289.1 |
| 8,507,266 B2 | 8/2013 | Welter et al. | |
| 2004/0219659 A1* | 11/2004 | Altman et al. | 435/284.1 |
| 2005/0112759 A1* | 5/2005 | Radisic et al. | 435/366 |
| 2007/0128715 A1* | 6/2007 | Vukasinovic et al. | 435/303.1 |
| 2007/0225597 A1* | 9/2007 | Banes et al. | 600/425 |
| 2009/0215104 A1 | 8/2009 | Taboas et al. | |
| 2011/0130310 A1 | 6/2011 | Schober et al. | |
| 2012/0035742 A1 | 2/2012 | Vunjak-Novakovic et al. | |

OTHER PUBLICATIONS

Altman, G., Horan, R.L., Martin, I., Farhadi, J., Stark, P.R.H., Volloch, V., Richmond, J.C., Vunjak-Novakovic, G., and Kaplan, D.L., "Cell Differentiation by Mechanical Stress", FASEB J. 16(2), 2002, pp. 270-272.
Altman, G.H., Stark, P., Lu, H.H., Horan, R.L., Calaro, T., Martin, I., Ryder, D., Richmond, J.C., Vunjak-Novakovic, G., and Kaplan, D.L., "Advanced Bioreactor with Controlled Application of Multi-Dimensional Strain for Tissue Engineering", Journal of Biomechanical Engineering 124, 2002, pp. 742-749.
Bancroft, G.N., et al., "Fluid Flow Increases Mineralized Matrix Deposition in 3D Perfusion Culture of Marrow Stromal Osteoblasts in a Dose-Dependent Manner", Proc Natl. Acad Sci U.S.A. 2002, 99(20); pp. 12600-12605.
Cannizzaro, C., Tandon, N., Figallo, E., Park, H., Gerecht, S., Radisic, M., Elvassore, N. and Vunjak-Novakovic, G., "Practical Aspects of Cardiac Tissue Engineering with Electrical Stimulation", Methods Mol Medicine, 2007, pp. 291-307.
Chao, PhG, Grayson, W. and Vunjak-Novakovic, G., "Engineering Cartilage and Bone Using Human Mesenchymal Stem Cells", Journal Orthop Sci 12(4), 2007, pp. 398-404.
Cimetta, E., Cannizzarto, C., Elvasore, N. and Vunjak-Novakovic, G., "Micro-bioreactor arrays for controlling cellular environments: Design principles for human embryonic stem cell applications," Methods 47, 2009, pp. 81-89.
Concaro, S., Gustavson, F., and Gatenholm, P., "Bioreactors for Tissue Engineering of Cartilage", Adv Biochem Eng Biotechnol, 2008, pp. 125-143.
Du, D., Furukawa, K., and Ushida, T., "Oscillatory Perfusion Seeding and Culturing of Osteoblast-like Cells on Porous Beta-tricalcium Phosphate Scaffolds", J. Biomed Mater Res A, 2008, 86(3): p. 796-803.
Figallo, E., Cannizzaro, C., Gerecht-Nir, S., Burdick, R., Langer, R., Elvassore, N. and Vunjak-Novakovic, G., "Micro-bioreactor Array for Controlling Cellular Microenvironments", Lab on a Chip 7 (6), 2007, Cover article, pp. 710-719.
Freed, L.E., Vunjak-Novakovic, G., and Langer, R., "Cultivation of Cell-Polymer Cartilage Implants in Bioreactors", J Cell Biochemistry 51, 1993, pp. 257-264.
Freshney, I., Obradovic, B., Grayson, W., Cannizzaro, C., and Vunjak-Novakovic, G., "Principles of Tissue Culture and Bioreactor Design", Principles of Tissue Engineering 3$^{rd}$ ed. (Lanza, Langer and Vacanti ed.) (2007), pp. 155-183.
Grad, S., et al., "Surface Motion Upregulates Superficial Zone Protein and Hyaluronan Production in Chondrocyte-Seeded Three-Dimensional Scaffolds", Tissue Eng. 2005, 11(1-2): p. 249-256.
Grayson, W.L., Bhumiranta, S., Cannizzaro, C., Chao, G.P., Lennon, D., Caplan, AL, and Vunjak-Novakovic, G., "Effects of Initial Seeding Density and Fluid Perfusion Rate on Formation of Tissue-Engineered Bone", Tissue Eng A, 2008, 14(11): 19 pages.
Grayson, W., Chao PhG, Marolt, D., Radisic, M., Cannizzaro, C., Figallo, E., and Vunjak-Novakovic, G., "Bioreactors for Tissue Engineering and Regenerative Medicine", Translational Approaches in Tissue Engineering and Regenerative Medicine Editors: Mao JJ, Vunjak-Novakovic, G., Mikos, A., and Atala, A., Artech House, Chapter 20, pp. 355-376 (2007).
Grayson, W.L., Chao, G.P., Marolt, D., Kaplan, D.L., and Vunjak-Novakovic, G., "Engineering Custom-Designed Osteochondral Tissue Grafts", Trends in Biotechnology 26(4), (2008), 16 pages.
Hung, C.T., et al., "A Paradigm for Functional Tissue Engineering of Articular Cartilage via Applied Physiologic Deformational Loading", Ann Biomed Eng., 2004, 32(1), pp. 35-49.
Lima, E.G., et al., "Functional Tissue Engineering of Chondral and Osteochondral Constructs", Biorheology, 2004, 41(3-4), pp. 577-590.
Liu, X.W.S., et al., "Quantification of the Roles of Trabecular Microarchitecture and Trabecular Type in Determining the Elastic Modulus of Human Trabecular Bone", Journal of Bone and Mineral Research, 2006, 21(1); pp. 1608-1617.
Mauck, R.L., et al., "Regulation of Cartilaginous ECM Gene Transcription by Chondrocytes and MSCs in 3D Culture in Response to Dynamic Loading", Biomechanics and Modeling in Mechanobiology, 2007, 6(1-2); pp. 113-125.
Mauck, R.L., et al., "Synergistic Action of Growth Factors and Dynamic Loading for Articular Cartilage Tissue Engineering", Tissue Engineering, 2003, 9(4), pp. 597-611.
Mauck, R.L., et al., "Functional Tissue Engineering of Articular Cartilage Through Dynamic Loading of Chondrocyte-Seeded Agarose Gels", Journal of Biomechanical Engineering, 2000, 122(3); pp. 252-260.
Meinel, L., et al., "Silk Based Biomaterials to Heal Critical Sized Femur Defects", Bone, 2006, 39(4); pp. 922-931.
Meinel, L., et al., "Silk Implants for the Healing of Critical Size Bone Defects", Bone, 2005, 37(5), pp. 688-698.
Meinel, L., et al., "Engineering Cartilage-like Tissue Using Human Mesenchymal Stem Cells and Silk Protein Scaffolds", Biotechnology and Bioengineering, 2004, 88(3), pp. 379-391.
Meinel, L., et al., "Engineering Bone-like Tissue in Vitro Using Human Bone Marrow Stem Cells and Silk Scaffolds", Journal of Biomedical Materials Research Part A, 2004, 71A(1), pp. 25-34.
Porter, B., et al., "3-D Computational Modeling of Media Flow Through Scaffolds in a Perfusion Bioreactor", Journal of Biomechanics, 2005, 38(3), pp. 543-549.
Radisic, M., et al., "Optical Mapping of Impulse Propagation in Engineered Cardiac Tissue", Tissue Eng Part A, 2008, pp. 851-861.
Radisic, M., Deen, W., Langer, R., and Vunjak-Novakovic, G., "Mathematical Model of Oxygen Distribution in Engineered Cardiac Tissue with Parallel Channel Array Perfused with Culture Medium Containing Oxygen Carriers", American Journal of Physiology 288, pp. H1278-H1289, 2005.
Radisic, M., et al., "Cardiac Tissue Engineering Using Perfusion Bioreactor Systems", Nat Protoc, 2008, 3(4), 40 pages.
Radisic, M., et al., "Functional Assembly of Engineered Myocardium by Electrical Stimulation of Cardiac Myocytes Cultured on Scaffolds", Pro Natl Acad Sci U.S.A., 2004, 101(52), pp. 18129-18134.
Searby, N.D., De Luis, J., Vunjak-Novakovic, G., "Design and Development of a Space Station Cell Culture Unit", SAE Transactions—Journal of Aerospace, 1998, pp. 1-13.
Seidel, J.O., Pei, M., Gral, M.L., Langer, R., Freed, L.E. and Vunjak-Novakovic, G., "Long-term Culture of Tissue Engineered Cartilage in a Perfused Chamber with Mechanical Stimulation", Biorheology 41 (3-4), 2004, pp. 445-458.
Sikavitsas, V.I., et al., "Mineralized Matrix Deposition by Marrow Stromal Osteoblasts in 3D Perfusion Culture Increases with Increasing Fluid Shear Forces", Proc Natl Acad Sci U.S.A., 2003, 100(25), pp. 14683-14688.
Tandon, N., et al., "Electrical Stimulation Systems for Cardiac Tissue Engineering", Nat. Protocols, 2009, 4(2), 32 pages.
Tandon, N., et al. "Design of Electrical Stimulation Bioreactors for Cardiac Tissue Engineering", Conf Proc IEEE Eng Med Biol Soc, 2008, 1, 10 pages.
Vunjak-Novakovic, G., De Luis, J., Searby, N., and Freed, L.E., "Microgravity of Cells and Tissues", Annals of the New York Academy of Sciences, 974: Microgravity Transport Processes in Fluid, Thermal, Materials and Biological Sciences, 2002, pp. 504-517.

(56) References Cited

OTHER PUBLICATIONS

Vunjak-Novakovic, G., Obradovic, B., Bursac, P., Martin, I., Langer, R., and Freed, L.E., "Dynamic Cell Seeding of Polymer Scaffolds for Cartilage Tissue Engineering", Biotechnology Progress 14, 1998, pp. 193-202.

Vunjak-Novakovic, G., Martin, I., Obradovic, B., Treppo, S., Grodzinsky, A.J., Langer, R., and Freed, L, "Bioreactor Cultivation Conditions Modulate the Composition and Mechanical Properties of Tissue Engineered Cartilage", Journal of Orthopedic Research 17, 1999, pp. 130-138.

Vunjak-Novakovic, G., "Functional Tissue Engineering of Cartilage: Scaffolds and Bioreactors", Tissue Engineering in Musculoskeletal Clinical Practice (ed. L.J. Sandell and A.J. Grodzinsky) Transactions of the American Academy of Orthopedic Surgeons, 2004, pp. 321-330.

Vunjak-Novakovic, G., Altman, G., and Kaplan, D., "Tissue Engineering of Ligaments", Annual Review of Biomedical Engineering 6, 2004, pp. 131-156.

* cited by examiner

BIOREACTOR, DEVICES, SYSTEMS AND METHODS

CROSS REFERENCE TO RELATED APPLICATIONS

This application claims the benefit of U.S. Provisional Application No. 61/267,405, filed on Dec. 7, 2009, and entitled "Bioreactor Devices, Systems, and Methods," the disclosure of which is incorporated herein by reference in its entirety.

STATEMENT REGARDING FEDERALLY SPONSORED RESEARCH

This invention was made with government support under grant number RR026244 awarded by the National Institute of Health (NIH). The government has certain rights in the invention.

BACKGROUND

The disclosed subject matter relates generally to devices, systems and methods involving bioreactions, for example, a controllable culture system (i.e., a bioreactor system) for study of human cells, such as stem cells, and/or engineered tissues, such as functional tissue graft bioreactors. More particularly, the disclosed subject matter relates to modular bioreactor devices, systems and methods.

SUMMARY

One or more embodiments of the disclosed subject matter include a bioreactor system having one or more bioreactor modules that can be individually controlled and identified. Each of the bioreactor modules can be connected to one or more functional modules such as a pump module, a stimulation signal generation module, a motor module, a mechanical transmission module, a gas exchange module, a temperature module, a humidity module and/or a $CO_2$ module, among others. The bioreactor and functional modules can include standard or universal connectors to facilitate connection and movement of modules. The bioreactor system can be controlled and/or monitored by a controller that can individually identify and control each connected module and that can be adapted to collect signal data from sensors embedded in any of the modules.

One or more embodiments of the disclosed subject matter can include: (i) a provision of controlled 3D environments resembling those encountered in vivo, (ii) application of multiple regulatory factors (e.g., molecular, physical, cell- and matrix-derived), (iii) modular designs for relatively high-throughput and combinatorial studies, and (iv) live imaging compatibility for real-time inspection and evaluation.

One or more embodiments of the disclosed subject matter also can include a bench-top bioreactor platform with culture modules each having, self-sustained cartridges (or functional modules) for medium flow, for example, and environmental control.

One or more embodiments of the disclosed subject matter additionally can include bioreactor configurations with medium perfusion, for example, and mechanical loading, suitable for studies of habitually loaded cells and tissues, for instance. One or more embodiments of the disclosed subject matter also can include bioreactor configurations with perfusion, electrical and mechanical stimulation, suitable for studies of electromechanically active cells and tissues, for instance.

Additionally, one or more embodiments of the disclosed subject matter can include a common platform which provides a set of functions that can be interfaced with on-line imaging, environmental control, and/or data acquisition.

One or more embodiments of the disclosed subject matter can combine different and optionally mutually exclusive provisions, such as (i) a provision of biologically relevant 3D environments, (ii) a modular design with the implementation of multi-parametric stimulation, and (iii) imaging compatibility and on-line data acquisition for real-time insight.

For example, a modular bioreactor system with a common bench-top platform housing all or substantially all technology required for different applications (e.g., pumps for perfusion, environmental control, mechanical actuators, electrical stimulator, etc.). Individual cartridges can be implemented and may be fully independent, self-sustained (with their own environmental control), and/or customized for a specific application. The cartridges can be coupled into modules of six, for example, and interfaced with on-line imaging, process control, and data acquisition.

As indicated previously, one or more embodiments of the disclosed subject matter can include a modular bioreactor platform with medium flow, for example, and environmental control, and the platform can be a common platform which can provide a set of functions, the ability to interface with on-line imaging and environmental control, and use of multiple modules having self-contained tissue culture cartridges, for example.

Also as indicated previously, one or more embodiments of the disclosed subject matter can include a bioreactor configuration with perfusion and mechanical loading, for example, for use in osteochondral tissue engineering. One or more embodiments of the disclosed subject matter additionally can include a bioreactor configuration with perfusion, electrical and mechanical stimulation (e.g., stretch). Also, the bioreactor platform can be modular and can be configured for perfusion, mechanical and electrical stimulation and can be for use in engineering of cardiac tissue constructs, for example.

Stimulation can include mechanical stimulation using a well-plate system with the application of mechanical stretch on the bottom membrane, for example; subjecting a single tissue sample to fluid flow and mechanical loading, adapted from vascular graft testing devices; a spinner flask (e.g., subjected to static or stirred medium); and rotating bioreactors (e.g., with multiple samples freely suspended in rotating flow).

One or more embodiments of the disclosed subject matter can include modules having one or more of the following features: individual medium/gas control, multiple samples, modular design, mechanical loading, electrical simulation, perfusion, and/or on-line imaging.

One or more embodiments of the disclosed subject matter can affect any of the following different areas of fundamental and translational research: (i) high throughput studies of human stem cells in 3D tissue settings, (ii) establishment of in vitro tissue-engineered models of disease; (iii) quantitative studies of the relationships between genes, exogenous factors and tissue function; (iv) investigations on how a cell makes decisions about differentiation-assembly-coupling into a tissue structure; (v) dynamic studies of cell responses to spatial and temporal gradients of regulatory molecules (e.g., Wnt); and (vi) enabling of "perturb and observe" experiments (e.g., introduce a new molecular species or cell phenotype and study cell-cell and cell-ECM interactions).

BRIEF DESCRIPTION

DETAILED DESCRIPTION

Figure 1:
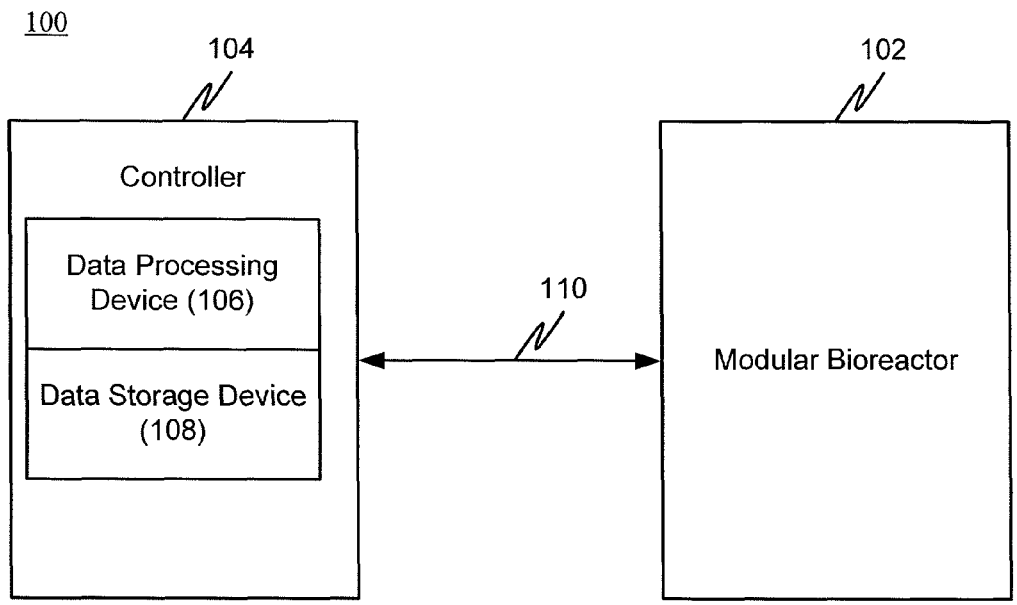
FIG. 1 is a diagram of a bioreactor system and controller in accordance with the present disclosure.

FIG. 1 is a diagrammatic view of a bioreactor system and controller in accordance with the present disclosure. In particular, a bioreactor system 100 includes a modular bioreactor 102 coupled to a controller 104 via an interface link 110. The controller 104 includes a data processing device 106 and a data storage device 108.

In operation, the bioreactions within the modular bioreactor 102 can be controlled, stimulated and monitored by the controller 104. Bioreactions can include engineering of tissues including, but not limited to, cardiac, cartilage, bone, ligaments and composite cartilage/bone grafts, osteochondral tissue or the like. In general, any bioreaction task suitable for carrying out within a bioreactor can be suited to an embodiment according to the present disclosure.

The controller 104 can include a programmable data processing device 106 (e.g., a microprocessor, microcontroller, digital signal processor, a desktop or portable personal computer, a netbook, personal digital assistant, tablet device, handheld wireless device or the like). The interface link 110 can include any wired or wireless link suitable for carrying signals between the bioreactor 102 and the controller 104. The controller 104 can also include one or more data storage devices 108 (e.g., flash memory, hard disk drive, CDROM, DVDROM or the like) to store software instructions for programming the data processing device and/or data received from the bioreactor 102 during monitoring.

The bioreactor 102 can include, for example, the following: an incubator-based modular bioreactor with medium flow and compressive loading for tissue engineering of cartilage; a modular bench-top bioreactor with medium flow and mechanical loading (tension, torsion) for ligament tissue engineering; bioreactor chambers housing up to six tissue constructs, with direct perfusion through the cultured constructs and imaging capability, for tissue engineering of bone; "smart well plates," a functionalized 6-well plate where the cover is replaced by a system enabling medium flow through each culture well, with precise control of hydrodynamic shear over cell monolayers; a modular bioreactor with perfused culture chambers fitted with the pairs of electrodes for electrical stimulation, for cardiac tissue engineering; a small-scale bioreactor system built by a combination of microfabrication and microprinting, for microarray cultures of cells in monolayers and thin gel settings; a modular bench-top bioreactor with medium perfusion and computer driven environmental control for cell culture at the International Space Station; a bioreactor with mechanical loading, for tissue engineering of cartilage; bioreactor with medium perfusion and mechanical loading; and a bioreactor for tissue engineering of anatomically correct osteochondral grafts. As discussed above, a bioreactor can, for example, be configured to resemble the size and shape of a 6-well plate.

The bioreactor 102 can include a common platform supporting cell or tissue cultivation in multiple independent modules (see, e.g., FIGS. 2-6 and corresponding description). The bioreactor 102 can be configured to a size and design conducive for bench-top work. In addition, the bioreactor can include a modular design, with individual modules composed of 6 self-contained cartridges, for example, in which each cartridge can be self-contained, with its own pump, gas exchanger and controls (see, e.g., FIG. 6). The cartridges can be manipulated (removed from the system, returned into the system) without disturbing culture or the operation of other cartridges (see, e.g., FIG. 5).

Figure 2:
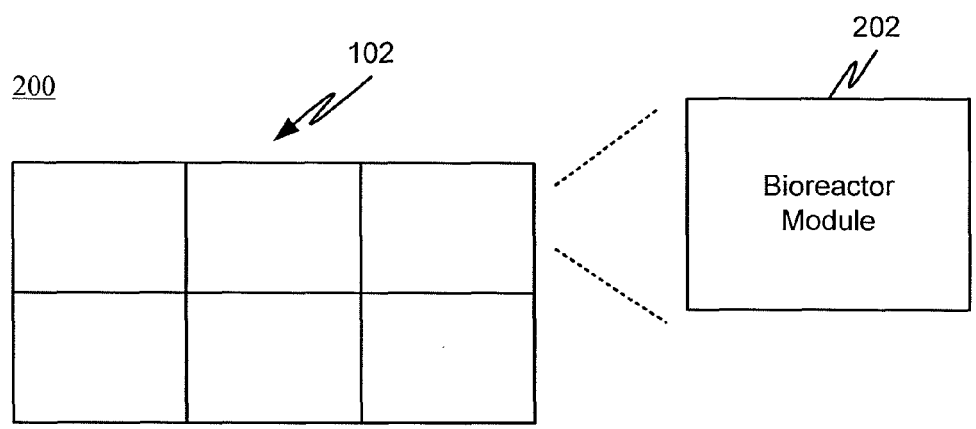
FIG. 2 is a diagram of a bioreactor system having multiple bioreactor modules in accordance with the present disclosure.

FIG. 2 is a diagram of a bioreactor system having multiple bioreactor modules in accordance with the present disclosure. In particular, the bioreactor system 200 includes the modular bioreactor 102 with six bioreactor modules 202.

Each bioreactor module can house a tissue construct (e.g., cardiac, bone, cartilage or other tissue) and can be configured as a cartridge that snap-fits together with other bioreactor modules. For example, each bioreactor module can be configured for direct perfusion through the cultured constructs and can include in place (or in situ) imaging capability, for tissue engineering of bone.

The bioreactor modules (or cartridges) 202 can be snap-fitted together into the modular bioreactor (102) as a set of six and placed into an incubator, for example. Also, each bioreactor module can be interfaced with on-line imaging, process control, and data acquisition modules or systems.

The assembled modules (or cartridges) can form a module housed within a mini-incubator, overlaid by an actuator platform and connected to outside controllers for management of the pumps, actuators, and electrodes. For example, a thin and transparent Indium Tin Oxide (ITO) film can be placed on the bottom of the mini-incubator and used to generate heat, and control temperature via thermocouple feedback loops. Each module can be designed to accommodate different types of tissues and biophysical stimulation regimes, within the same universal framework of bioreactor according to the disclosed subject matter. A temperature-controlled incubator can be fitted with small gas tanks and a small temperature controller to facilitate its transport between the bench top and another testing area (e.g., live µCT imaging), and returned without disrupting culture. The cartridges can connect via a snap-fit design and can detach without disrupting remaining cartridges.

Figure 3:
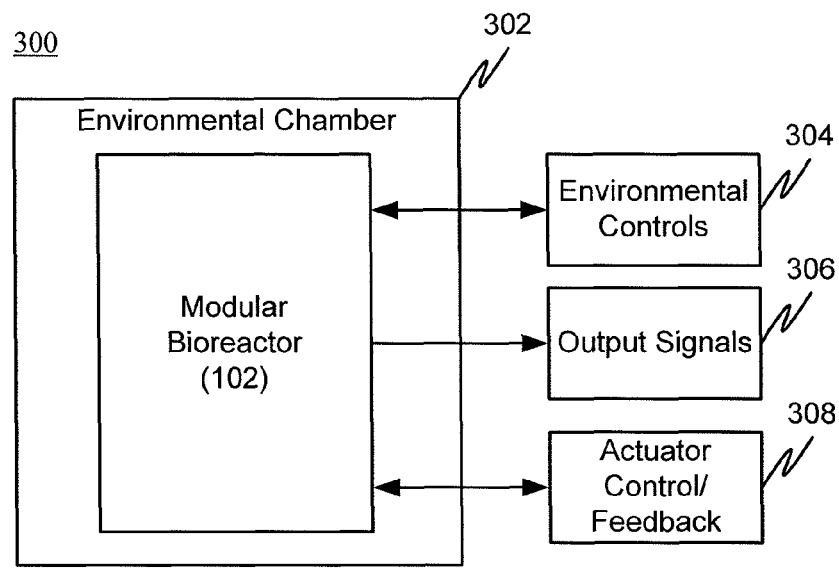
FIG. 3 is a diagram of a bioreactor system having an environmental chamber in accordance with the present disclosure.

FIG. 3 is a diagram of a bioreactor system having an environmental chamber in accordance with the present disclosure. The bioreactor system 300 includes the modular bioreactor 102 disposed within an environmental chamber 302. The modular bioreactor 102 includes connections for environmental controls 304, output signals 306, and actuator control/feedback signals 308.

The environmental controls 304 can include electrical signals for controlling environmental systems coupled to the environmental chamber, and/or conduits for gas exchange to control temperature, humidity and/or gas concentration (e.g., $CO_2$ level) within the environmental chamber 302. The output signals 306 can include electrical signals, image signals or the like transmitted from sensors in or near the environmental chamber 302. The actuator control/feedback signals can include signals for controlling the movement of one or more actuators (e.g., mechanical actuators) and for receiving feedback from the actuators or sensors measuring actuator parameters. The environmental controls 304, output signals 306, and actuator control/feedback signals 308 can be configured to control the modular bioreactor 102 as a whole unit or to control each bioreactor module within the modular bioreactor 102.

Figure 4:
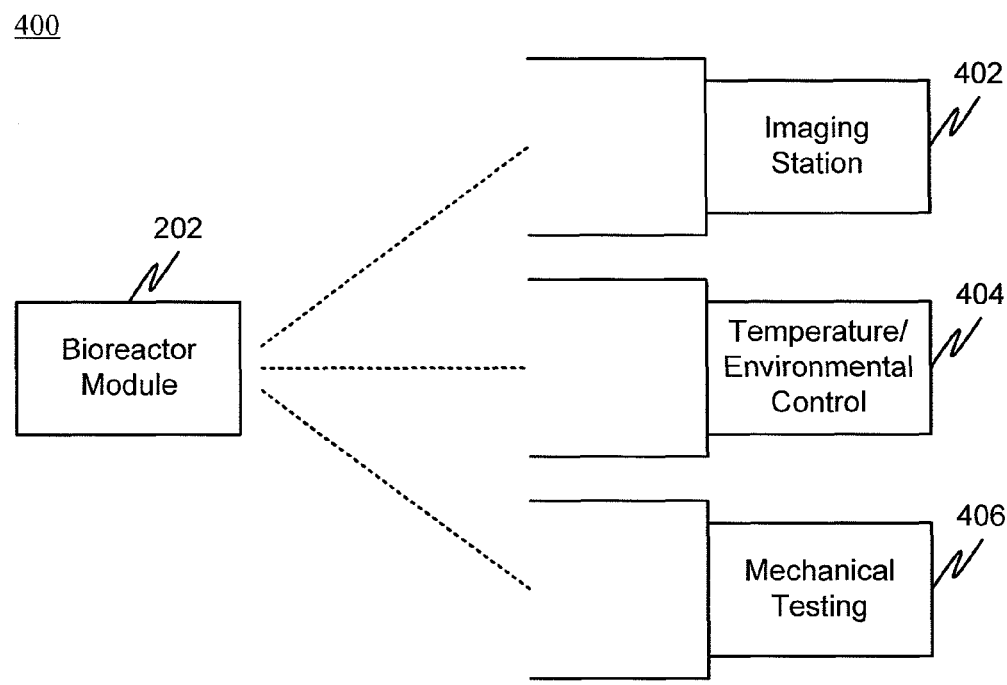
FIG. 4 is a diagram of a bioreactor system showing imaging, environmental and mechanical testing stations in accordance with the present disclosure.

FIG. 4 is a diagram of a bioreactor system showing imaging, environmental and mechanical testing stations in accordance with the present disclosure. In particular, the system 400 includes a bioreactor module 202 that is mechanically adapted to be connected with an imaging station 402, a temperature/environmental control 404 and a mechanical testing station 406.

In operation, the bioreactor module 202 can be connected to the temperature/environmental control 404 system for sustaining or growing tissue, for example. To monitor the growth of the tissue, the bioreactor module 202 can be removed from the temperature/environmental control 404 system and connected to the imaging station 402. The imaging station can include a device such as a microscope or video camera adapted to capture an image of a tissue sample within the bioreactor module 202. The bioreactor module can be disconnected from the temperature/environmental control 404 system or the imaging station 402, and connected to the mechanical testing station 406. The mechanical testing station can include devices and sensors for performing a mechanical test on the tissue sample within the bioreactor module 202.

The bioreactor module 202 can include standard or universal connectors to permit the module to be easily connected to other modules or systems. Also, the universal connectors can permit easy electrical, fluid or mechanical connection and disconnection between bioreactor modules and other modules or equipment. The imaging station 402, the temperature/environmental control 404 system and the mechanical testing station 406 can each have universal connectors that correspond to (and mate with) the connectors on the bioreactor module 202.

Figure 5:
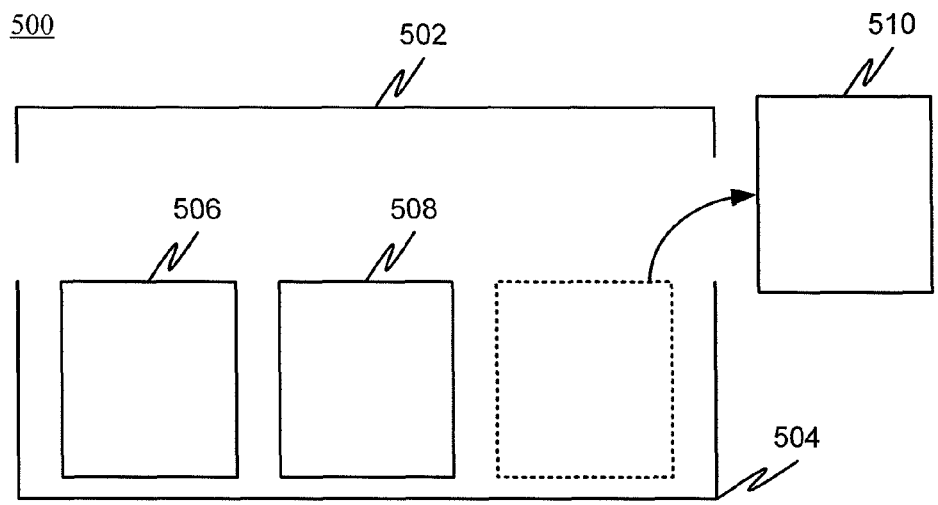
FIG. 5 is a diagram of a bioreactor system showing a plurality of modules within a bioreactor system, with each module being individually removable, in accordance with the present disclosure.

FIG. 5 is a diagram of a bioreactor system showing a plurality of modules within a bioreactor system, with each module being individually removable, in accordance with the present disclosure. The bioreactor system 500 includes a lid 502 removably connectable to a base 504. The lid 502 and base 504 can be coupled to form an essentially sealed unit housing two bioreactor modules 506 and 508. A third bioreactor module 510 is shown removed from the unit formed by the lid 502 and base 504. Removal of the third bioreactor module 510 does not disturb the other two bioreactor modules (506 and 508), which can continue in a cell culture, tissue study or tissue engineering process.

Figure 6:
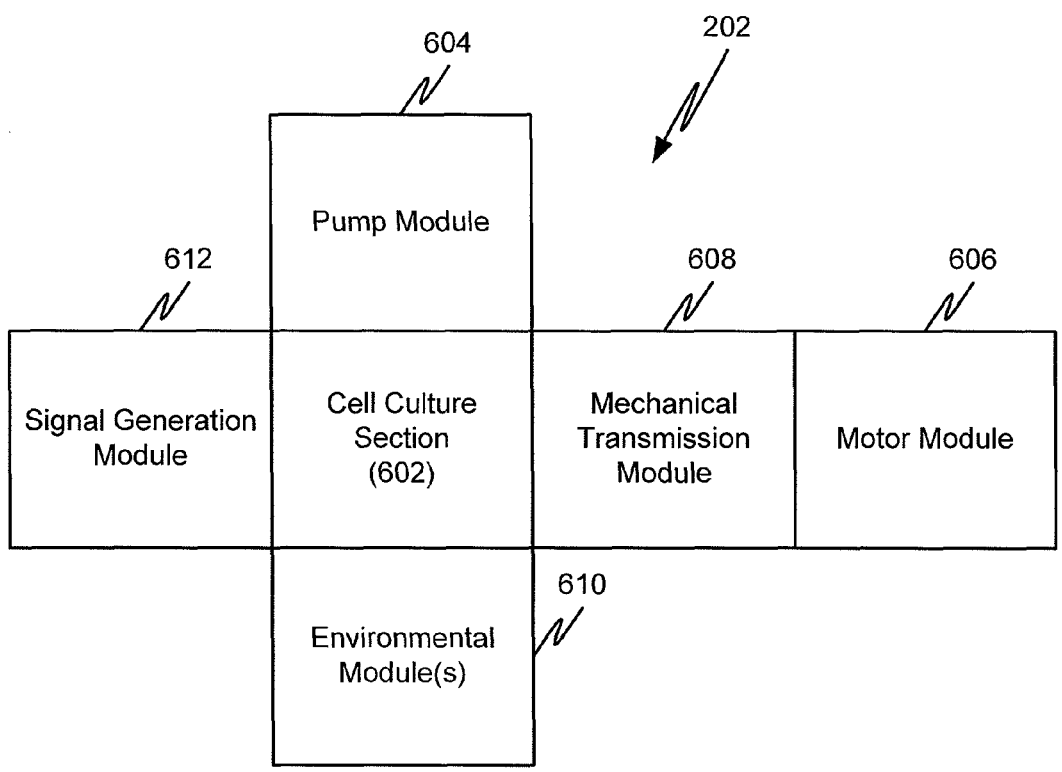
FIG. 6 is a diagram of a bioreactor module showing a cell culture section and a plurality of functional modules in accordance with the present disclosure.

FIG. 6 is a diagram of a bioreactor module showing a cell culture section and a plurality of functional modules in accordance with the present disclosure. In particular, the bioreactor module 202 includes a cell culture (or cell study or tissue engineering) section 602, a pump module 604, a motor module 606, a mechanical transmission module 608, one or more environmental modules 610 and a signal generation module 612.

The cell culture section 602 can be implemented as a cartridge that has an interior suited to the type of cell or tissue process to be performed and having an exterior that is standard or common, such that the functional modules can be mechanically and electrically connected. Further, a bioreactor module 202 can be configured as a custom-designing tissue culture cartridge having standardized exterior features that permit the module to be integrated with a bioreactor platform (or system).

In operation, cells or tissue being cultured in the cell culture section 602 can be perfused with chemical treatments (e.g., nutrients, dissolved gases, etc.) using the pump module 604. The pump module 604 can be selected for a desired flow range or other characteristics from a variety of pump modules. The pump module 604 can be selected based upon the type of cell culture, cell study or tissue engineering process being carried out. Medium perfusion—through each cell culture section 602 (or cartridge) independently—can be provided, via the pump 604, as a baseline feature and utilized for gas/medium exchange.

The cells or tissue contained in the cell culture section 602 can be subjected to mechanical stimulation and loading using the combination of the motor module 606 and the mechanical transmission module 608. Forces produced by the motor module 606 can be transmitted to the cell culture section 602 via the mechanical transmission module 608. The mechanical transmission module 608 can include devices for mechanical transfer such as rotational, linear Z, planar XY, or a combination of the above. The motor module 606 can be selected for speed and power applicable to the cell culture, cell study or tissue engineering process being carried out.

The one or more environmental modules 610 can include a combined module or separate modules for temperature, humidity, gas exchange, $CO_2$ and/or the like. The signal generation module 612 can include devices for generating stimulation signals such as electrical, light, acoustic, ultrasonic, and the like, or a combination of one or more of the above.

The bioreactor module 202 can be configured such that imaging, either continuous or discrete, can be readily obtained. The module may be configured to be placed into an imaging device (e.g., a microscope). Or, alternatively, the bioreactor module 202 can be configured such that an imaging device (e.g., a digital image sensor) can be attached to the bioreactor module to obtain images continuously or as desired during the cell culture, cell study or tissue engineering process. Thus, an image record of the cell culture, cell study or tissue engineering process can be obtained.

The bioreactor 202 of FIG. 6 is shown highly diagrammatically for illustration and explanation purposes. It will be appreciated that a different number of modules may be connected to the cell culture section 602 and that the modules may be arranged in different orientations than those shown in FIG. 6. In general, the number, type and placement of modules may be based on a contemplated cell culture, cell study or tissue engineering process.

A bioreactor using modules such as that described in FIG. 6, can provide (i) precise control of cell/tissue environments, (ii) multi-parametric signaling (e.g., hydrodynamic, mechanical, electrical) applied in concert with molecular regulatory factors, and (iii) imaging capability.

For example, to engineer osteochondral grafts, in addition to perfusion required for bone, the bioreactor 202 can be configured to apply mechanical loading (via the motor module 606 and mechanical transmission module 608) to the cartilage layer of the graft.

To engineer cartilage, bone, ligaments and composite cartilage/bone grafts, the bioreactor 202 can be configured with functional modules to provide multiparametric stimulation, for example. To engineer cardiac tissues, the cell culture section 602 can provide for cultivation of cells on scaffolds with an array of channels (provided to mimic the capillary bed) that can be perfused with culture medium supplemented with oxygen carriers (to mimic hemoglobin capacity for oxygen) via the pump module 604, for example.

The bioreactor module 202 can be sized according to the requirements for a particular cell or tissue process. For example, a small-scale microarray bioreactor optionally may be implemented.

As discussed above, the bioreactor 202 can provide environmental control (e.g., by controlling medium composition and flow in bench-top environmental chambers) via the one or more environmental modules 610.

A modular bioreactor (e.g., 102) including one or more bioreactor modules 202, as indicated above, can provide a standardized platform for the integration of multiple functions (e.g., application of hydrodynamic and mechanical electrical signals. The modular bioreactor can provide flexibility in design and operation through the ease of connecting or disconnecting functional modules that can be selected from a variety of functional modules. Also, as discussed above, the bioreactor modules 202 can provide imaging compatibility for direct insight into the dynamics of cellular processes via the modular design adapted for use with an imaging device.

A bioreactor, in accordance with the present disclosure, can include a common platform providing a set of functions (e.g., medium perfusion, environmental control, interfaces with imaging, data acquisition, etc.) and accommodating multiple modules (e.g., 202) having of self-contained tissue culture cartridges (e.g., 602). The design of the overall platform and the exterior of the modules and cartridges (including their dimensions and connection ports) can be standardized. In addition to the above set of functions, which can facilitate the cultivation of any biological 2D or 3D construct irrespective of cell or tissue phenotype, the platform can be designed to enable various types of multiparametric stimulation of cultured tissues, by mechanical and electrical signals, for example.

The bioreactor module 202 can be individually addressable (e.g., via Internet Protocol address, radio frequency identification (RFID) tag, bar code, or the like) and controllable by a controller (e.g., 104) that includes custom-designed software for multiparametric regulation of the bioreactor.

Cartridge (e.g., cell culture section 602) characteristics can include fixed external dimensions, standardized design and/or standard positions of fluid ports. The cartridge can be formed from transparent material compatible with microscopy and μCT imaging. The cartridges can include customization of internal design features to accommodate various experimental designs. Also, cartridges can be transported in environmental containers to other locations (e.g., for specialized measurements).

Environmental control can include constant perfusion (e.g., 0.01-1 mL/min per cartridge), temperature (e.g., 36° C.-38° C.), pH (e.g., 7.2-7.6), Humidity (e.g., >95%), gas mixture (any mixture since each cartridge can receive its own gas supply).

Manipulation and sampling can include: addition of supplements or sampling of medium throughout culture; on-line measurement of oxygen and pH within the cartridges; individual cartridges can be removed (e.g., for imaging) and returned without stopping the flow or disturbing the operation of other cartridges.

Biophysical stimulation can include: dynamic axial compression (e.g., 0.1-25% strain; strain or force control, any regime of application). Electrical stimulation can include signal amplitude (e.g., 0.1-10 V/cm), frequency (e.g., 0.05-20 Hz), and any wave form or regime of application. Biochemical stimulation can include combinations of regulatory molecules, supplementation of factors at any time during culture. Control and data acquisition can include control of flow, oxygen concentration, medium exchange, electrical and mechanical stimuli, in-line sensors for oxygen, pH and temperature, sampling and exchange of medium in individual cartridges, real time imaging (microscopy, μCT).

Figure 7:
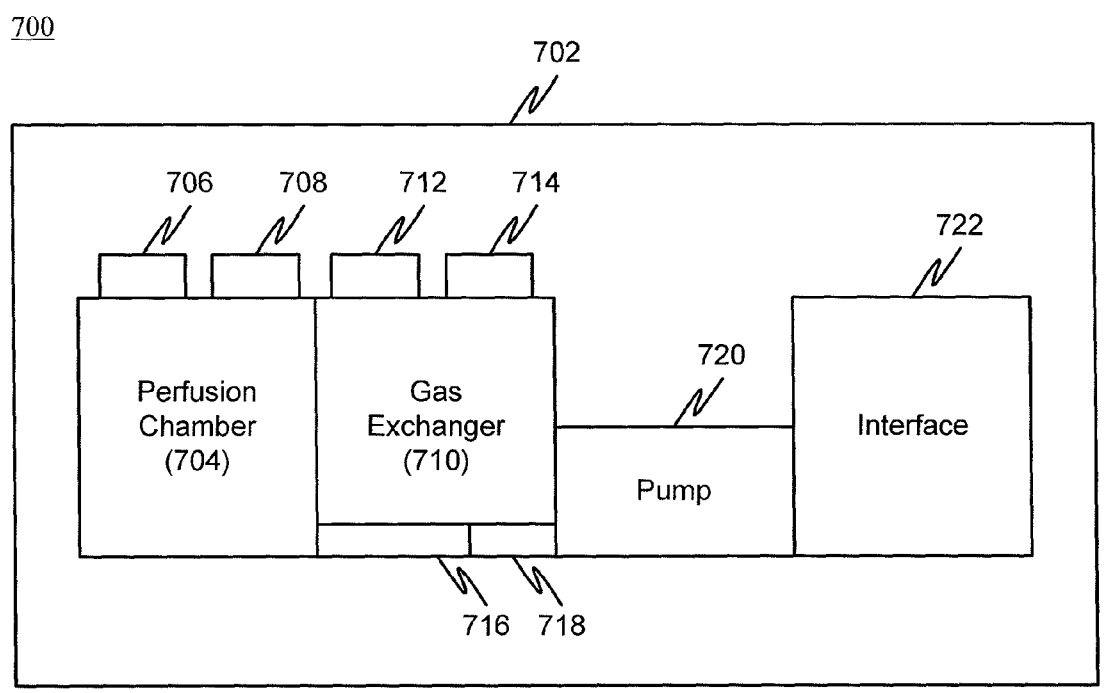
FIG. 7 is a diagram of a bioreactor cartridge in accordance with the present disclosure.

FIG. 7 is a diagram of a bioreactor cartridge (or module) in accordance with the present disclosure. In particular, a bioreactor cartridge 700 includes a perfusion chamber 704 with a loading post 706 and a cell seeding port 708, a gas exchanger 710 having a gas inlet port 712 and a gas outlet port 714, medium transfer conduits 716, a sampling port 718, a pump 720 and an interface 722.

Each cartridge 700 can be individually designed to achieve the desired biophysical stimulation but still have an overall shell (or outer shape) design that can remain within a common frame layout for compatibility with a temperature controlled incubator and a mechanical testing unit.

Medium can be added or removed as well as samples collected via the sample collection port 718 disposed at an outlet connection 716 of the perfusion chamber 704. Also, a humidified $N_2/O_2/CO_2$ mixture of a desired composition (which can vary from one cartridge to another) can be supplied to each cartridge via the gas exchanger 710. Cells or medium can also be added from a top port 708 located on the lid of the perfusion chamber 704. Optical oxygen sensors and pH sensors can be placed as needed in-line with conduits 716 between the perfusion chamber 704 and the sample port 718 for data collection. The cartridge 700 can be designed to hold the tissue/construct sample within the focal length of commonly used microscopy tools, and allow the use of 2x-10x objectives of inverted microscopes. The cartridge 700 (without the pump and electronics) and all tubing material can be compatible with steam and ethylene oxygen sterilization.

A temperature control incubator designed to hold a bioreactor having one or more cartridges (e.g., environmental chamber 302), a gas exchanger (coupled to the incubator or each cartridge), and each cartridge 700 can be thoroughly validated after manufacture. As part of the validation of the system, the gas exchanger unit (e.g., 710) can be fitted with in-line optical oxygen monitors and flow meters at the inlet and outlet gas connections (712, 714), and the mass transport can be experimentally determined for varying flow rates and gas mixtures. The optimum configuration of gas flow rates, tubing length, and tubing thickness for each cartridge design can be determined to accommodate the perfusion rates needed during culture. This can help ensure the maintenance of the target oxygen conditions in medium (hypoxia, hyperoxia, normoxia) during the culture period. Concurrently, temperature can be monitored within the cartridge 700. Cartridges can be tested to ensure that the samples can be viewed without difficulties under the microscope by light and fluorescent microscopy. Cartridges that make use of actuators for mechanical stimulation can be tested to ensure appropriate transfer of movement between an actuator (not shown) and the loading post 706.

Figure 8:
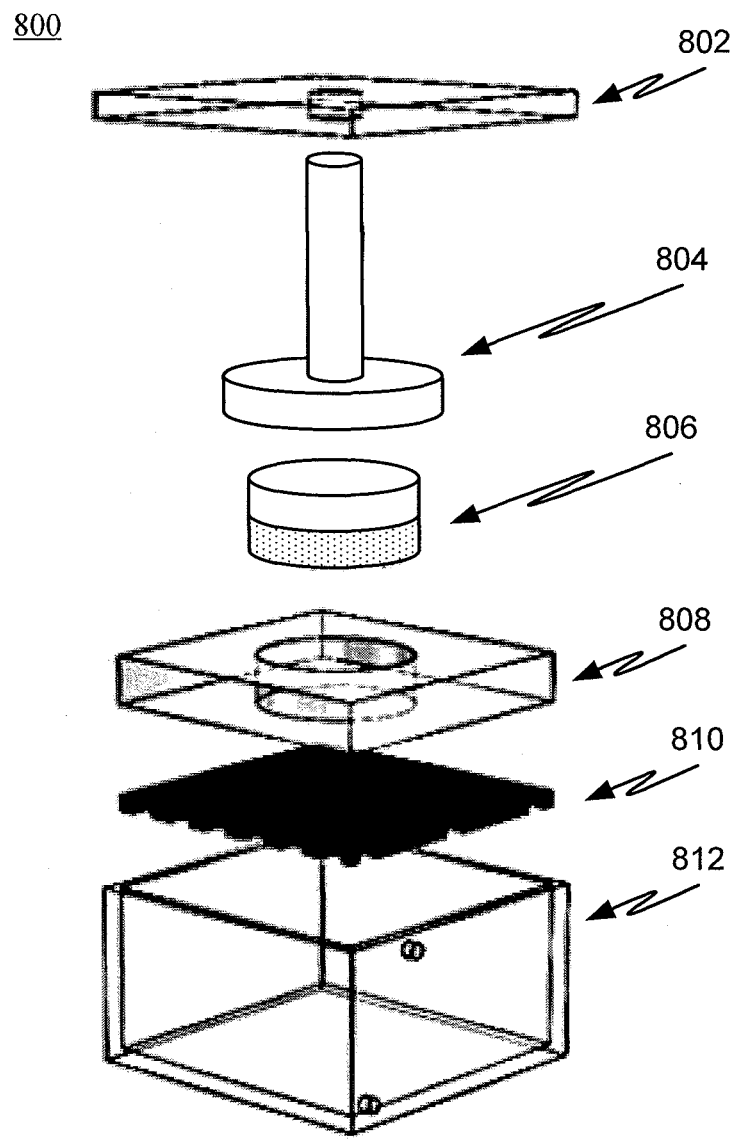
FIG. 8 is an exploded diagram of a perfusion chamber for a bioreactor cartridge in accordance with the present disclosure.

FIG. 8—are diagrams showing a perfusion chamber for a bioreactor cartridge in accordance with the present disclosure. In particular, FIG. 8 is a diagrammatic, exploded view of a perfusion chamber 800. The perfusion chamber 800 includes a cover 802, a loading platen 804, a tissue scaffold 806, a polydimethylsiloxane (PDMS) gasket 808, a porous platen 810 and a module container 812.

In operation, the loading platen 804 can be connected to an external actuator having capability, for example, for axial motion (to apply compression) or oscillatory rotation around the vertical axis (to apply torsional shear) to the tissue scaffold 806. The tissue scaffold 806 (e.g., a bone or tissue graft) can be supported in the PDMS gasket 808. The porous platen 810 can be designed to provide three different functions, for example: (i) to support the compressive forces, (ii) to prevent the tissue scaffold 806 from slipping under torsional shear, and (iii) to provide even distribution of culture medium flowing through the tissue scaffold 806.

The PDMS gasket 808 can include a channeled PDMS mold cast with a silicone elastomeric base and cured at 600° C. for 4 hours, or other appropriate cure temperature and time. For example, the height of the PDMS mold can be 1-2 mm lower than that of the bone region of graft to allow the fluid to flow in. Depending on the construct size, the number and spacing of the channels may be changed accordingly.

Driven by a pump (e.g., 720) attached to the cartridge, culture medium conditioned in the gas/medium exchanger (e.g., 710) can be directed into the cartridge 800 and through the tissue scaffold 806 (or tissue construct), and exit via the outlet at the bottom of the cartridge. Tissue constructs can be tightly fitted into the wells of the pre cast PDMS mold, to prevent medium from flowing around the constructs. For example, in contrast to bone, which has large interconnected pores and large void volume, engineered cartilage has low permeability, such that the culture medium can flow around the cartilage and through the bone.

For mechanical loading, the tissue construct can be preloaded between the top (movable) platen 804 and the bottom (fixed) platen 810 to ensure full contact and prevent slip during torsion. Depending on the exact loading requirements, dynamic compression and torsional shear can be applied individually or sequentially. The tissue scaffold 806 can include a cartilage portion disposed on top of a bone portion. The engineered cartilage portion of the tissue scaffold 806 can extend above the PDMS gasket 808, its lateral expansion under axial compression results in laterally unconfined compression, with tension at the periphery that closely resembles physiological loading. The system design can be modified to provide confined compression, which is in turn associated with uniform stress throughout the construct. The torsional configuration provides dynamic shear stresses and strains (i.e., pure shear) and can avoid the non-uniform axial compressive stress associated with the simple shear generated by a system of parallel plates. An embodiment of the disclosed subject matter can permit studies of both the individual and synergistic effects of compressive and shear stresses on tissue growth, as well as the dose effects of loading time, frequency and amplitude.

The cartridge 800 can be sealed and the gas exchange confined to the adjacent gas/medium exchange chamber (e.g., confined between 704 and 710). A flexible membrane disposed between the loading platen shaft and the cover of the cartridge can ensure minimal gas leakage. As discussed above, medium can be withdrawn for sample collection and medium exchange at the outlet port (so that the cartridge contents is sampled) using a syringe, and flow-through oxygen and pH sensors can be added on to the outlet for real-time measurement of oxygen consumption and monitoring of pH.

An individual cartridge 800 can be separated from other cartridges or a system as described earlier. Because each cartridge can have its own gas/medium exchange chamber and peristaltic pump, the cartridges can be self-sustainable. Therefore it is possible to carry an individual cartridge to high-resolution imaging facilities (MRI, μCT or ultrasound) to monitor and evaluate tissue growth.

Medium perfusion through the porous scaffold (e.g., 806) can enable adequate nutrient transport and imparts shear stress directly onto the cells within the scaffold. Computational modeling of flow through the constructs can be effectively used to estimate the levels of shear and determine suitable operating flow rates. These values, however, can be highly dependent on the internal geometry of the scaffolds. Modeling has demonstrated that superficial fluid velocities of 100-400 pm/s through trabecular bone constructs correlated with the shear stress of 1-10 mPa. Alternatively, flow-rates may be determined empirically by evaluating cell growth, viability and distribution as a function of medium flow-rate.

The loading platen 804, when connected to an actuator, allows both the translational and rotational movement to provide compressive and torsional loading. Application of dynamic loading may require initial offset so that the loading platen 804 remains in contact with the tissue scaffold 806 during the loading cycle. Dynamic compression has been widely shown to enhance the cartilage development in tissue engineering. For example, with frequencies of 0.0001 (static)-3 Hz (supra-physiological), compressive stresses exerted on the scaffolds of 0.1-24 Mpa, and strain levels of 0.1-25%. A representative loading protocol involves sinusoidal dynamic compression at a 10% peak-to-peak compressive strain, at a frequency of 1 Hz, applied for 3-5 days a week, for 3 hours per day.

The cartridge 800 can support concurrent perfusion and loading. An actuator can be controlled with high accuracy via a computer program running on a controller (e.g., 104) coupled to the actuator that can be set to provide compression, shear or a combination thereof, with any loading protocol of interest (strain, frequency, cycle duration, time of the day). A force transducer may be added to the system (e.g., under the actuator) to offer real time force measurement throughout the cultivation period, which would provide a system for monitoring tissue development.

Figure 9:
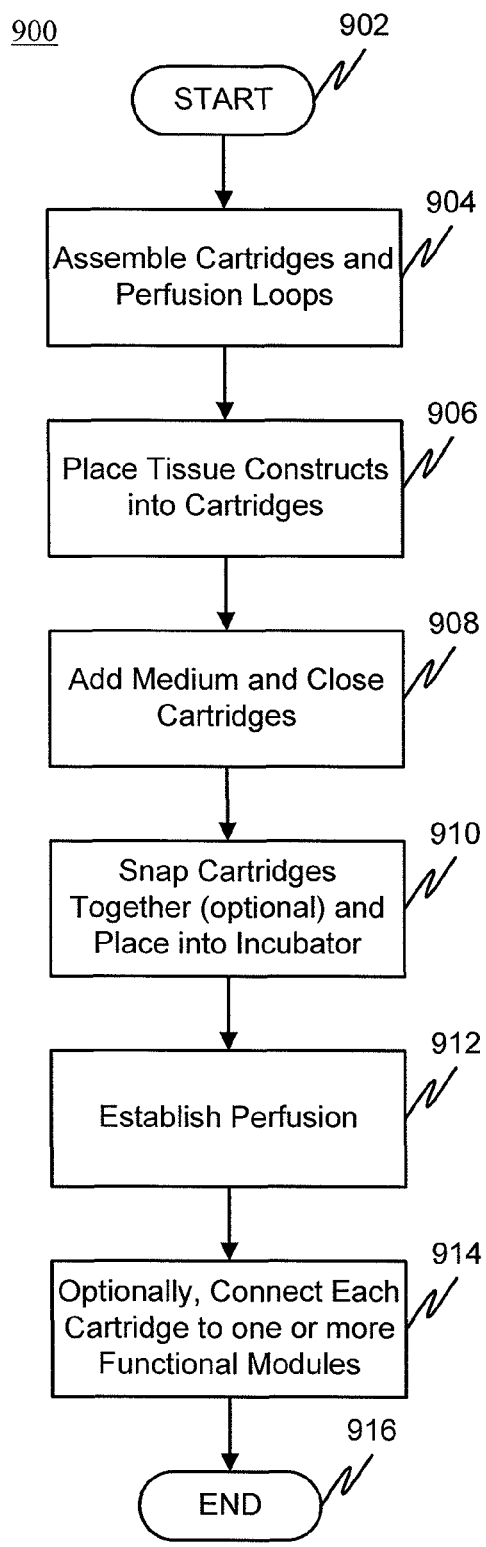
FIG. 9 is a chart showing a method of cell or tissue culture using a bioreactor in accordance with the present disclosure.

FIG. 9 shows a chart of a process for setting up and operating a bioreactor according to the present disclosure. In general, constructs (or scaffolds) may be seeded within the cartridge (using perfusion depth-filtration) or external to the cartridge. The setup of the bioreactor may be a multi-step process. The process 900 begins at 902 and continues to 904.

At 904, cartridges and perfusion loops are assembled. Fully assembled cartridges can be steam-sterilized. A gas exchanger and pump can be connected to a sterile cartridge. The process continues to 904.

At 904, the tissue construct(s) can be press-fitted into the PDMS wells inside the cartridges. This step can be performed in a laminar flow hood. The process continues to 906.

At 906, the cartridges are filled with culture medium and the chamber is closed. If mechanical loading is required, a cover with an attached platen can be used. The platen may be set to touch the top surface of the tissue construct. The process continues to 908.

At 908, assembled cartridges are snapped together and placed into "mini incubators," which maintain appropriate or suitable environmental conditions for the constructs. The process continues to 910.

At 910, perfusion is established. The process continues to 914.

At 914, each cartridge can be connected to one or more functional modules to provide electrical or mechanical stimulation. The process continues to 916, where the process ends.

The system can be designed to support long-term (e.g., weeks to months) operation under sterile conditions. Using samples collected during medium exchange, one can measure lactate production and glucose consumption, or tissue-specific proteins (such as the superficial zone protein released by cartilage in response to shear).

Figure 10:
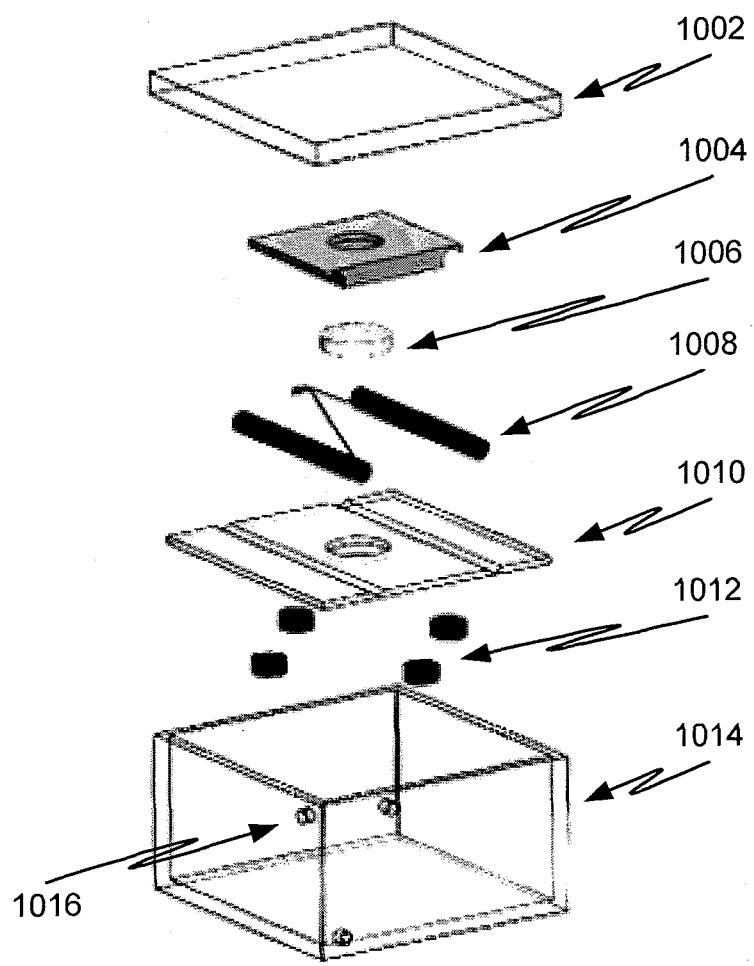
FIG. 10 is an exploded diagram of a bioreactor cartridge for perfusion and electrical stimulation in accordance with the present disclosure.

FIG. 10 is an exploded diagram of a bioreactor cartridge for perfusion and electrical stimulation in accordance with the present disclosure. In particular, a cartridge 1000 includes a cover 1002, an alignment cover 1004, a tissue scaffold 1006, electrodes 1008, a PDMS gasket 1010, standoffs 1012 and a bottom cover 1014.

In operation, tissue constructs or scaffolds 1006 can be either internally or externally seeded. For example, a high-efficiency seeding process for cardiac tissue constructs prior to insertion into bioreactor can be provided. Cartridge 1000 preparation can involve fitting the electrodes 1008 into the cartridge 1000, connecting the wires of the electrodes 1008 to the data port 1016 of the bottom cover 1014, and assembling the culture chamber, gas exchange chamber, and tubing together into a single cartridge autoclaved for sterility. The pump is then inserted, culture medium is pre-filled into the culture chamber, a tissue scaffold 1006 construct is placed on top of the lumen in the PDMS gasket 1010, and the pre-sterilized PDMS gasket 1010 is placed on top of the tissue scaffold 1006. The cartridges can then be snap-fitted into modules of six, and each module can be placed into the mini-incubator as described above. Medium perfusion can be initiated at a flow rate providing hydrodynamic shear, at the channel lumens <2.4 dyn/cm2. For example, electrical stimulation can be applied after three days of cultivation, for an additional 5 days, with voltage amplitudes 8 V/cm.

Figure 11:
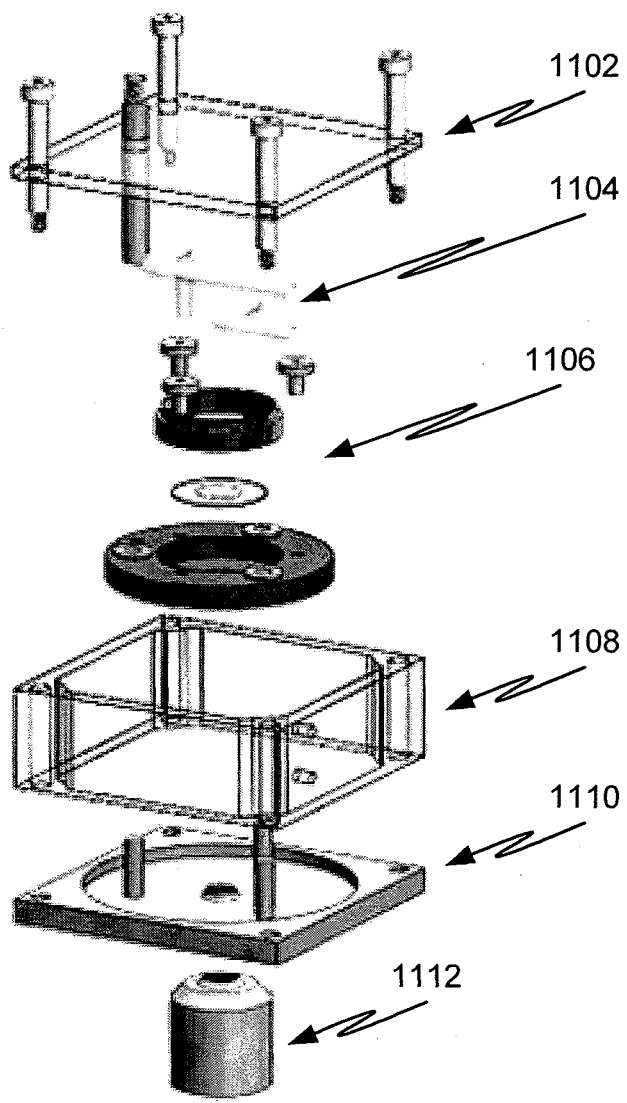
FIG. 11 is an exploded diagram of a bioreactor cartridge for perfusion and mechanical stimulation in accordance with the present disclosure.

FIG. 11 is an exploded diagram of a bioreactor cartridge for perfusion and mechanical stimulation in accordance with the present disclosure. In particular, the cartridge 1100 includes a cover 1102, perfusion tubing 1104, tissue scaffold and PDMS layer 1106, module container 1108, indenter 1110 and objective 1112.

In operation, the cartridge 1100 can provide a platform for the culture of cells on a thin membrane scaffold subject to periodic isometric strain and medium perfusion across the membrane. The cartridge 1100 can include an indenter 1110 with vertical pillars disposed on the base of the cartridge. There can be an inlet on the top of the cartridge, which can interface the actuator and scaffold-ring, as well as two ports for the medium inlet and outlet. A tissue scaffold can be loaded into a PDMS gasket device to form an assembly 1106 that holds the tissue scaffold in place over the indenter 1110. The indenter (or base plate) can be made of stainless steel and can sit beneath a sterile barrier (PDMS membrane) on top of which the scaffold 1106 is placed. The three layers 1106 can be compressed by an additional ring and the scaffold holding device is screwed together to ensure the scaffold remains in place. This ring setup may have three holes to fit the three pillars on the cartridge, as well as a port to interface with the actuator, housed externally.

At rest position, the scaffold 1106 can sit directly over the indenter at zero strain. The actuator can move the device up/down along the three-pillared track. The tissue construct can be preloaded to ensure full contact and prevent slip during stretch. As the construct moves, it is pushed over the indenter, and generates isometric stretch. The indenter 1110 is hollow and adapted to the shape of a microscope objective, to allow for high magnification imaging at short focal lengths while undergoing mechanical stimulation. The movement of the scaffold 1106 over the indenter 1110, and not the reverse, allows the scaffold 1106 to remain within the same plane of view throughout imaging. Medium perfusion can be established through the cartridge, and across the scaffold surface.

For example, to assemble this type of the cartridge, a 1.5 cm diameter scaffold can be placed over a PDMS membrane, which acts as a barrier between the indenter and tissue. The two are then placed over a ring and held in place using a second ring that is screwed in place, compressing the tissue's border, and leaving a 1 cm diameter piece of tissue exposed. The whole construct is mounted onto the three pillars that rest on the bottom of the cartridge and act as a guide for vertical translation of the tissue. The actuator is interfaced to the ring via an adapter port on the top of the cartridge. At rest, the scaffold is now resting over the indenter, placed at the bottom face of the cartridge. The actuator can cause vertical motion of the ring, pushing it over the indenter, and resulting in isometric strain of the tissue. Only the scaffold ring is filled with culture medium (PDMS membrane in ring prevents media from flowing through), which is perfused over the construct as described above. For instance, dynamic stretch can be applied at a strain of 10% and a frequency of 1 Hz, for up to 10 days, with online assessment capabilities.

Contractile activity of live engineered cardiac constructs is routinely assessed by measuring the change in construct size in response to electrical field stimulation. The cartridge can be disconnected and moved to a microscope with temperature control, where it is then connected to a cardiac stimulator, and responses to electrical stimuli can be measured. To assess contractile force of the generated cardiac constructs in response to electrical stimulation, we can use our custom-built force-transducer (e.g., with a range of 0-10 mN, sensitivity of 1 μN), under sterile and temperature and pH controlled conditions.

Further, thin cardiac tissue constructs (e.g., 500 pm-1 mm) may be cultured under physiological strain with perfusion of medium, and online imaging. Assessment of the contractile activity may be achieved via force transduction as described above, or through the analysis of strain measured by imaging. The cartridge 1100 has the unique ability to fit onto a standard microscope objective, allowing for high magnifications (e.g., up to 40×) that allow for imaging of single cells. Strains at the single cell level may be determined by taking the cartridge to a microscope stage. Additionally, voltage sensitive dyes can be used for live imaging of electrical signal propagation.

It is, therefore, apparent that there is provided in accordance with the present invention, bioreactor devices (or apparatus), systems and methods. While this invention has been described in conjunction with a number of embodiments, it is evident that many alternatives, modifications and variations would be or are apparent to those of ordinary skill in the applicable arts. Accordingly, applicants intend to embrace all such alternatives, modifications, equivalents and variations that are within the spirit and scope of this invention.

The invention claimed is:

1. A modular bioreactor system comprising:
   a controller having a data processing device and a computer readable medium, the computer readable medium having stored thereon software instructions that, when executed by the data processing device, cause the data processing device to perform operations including controlling the bioreactor system and acquiring data from the bioreactor system;

one or more bioreactor modules together forming a modular bioreactor, each bioreactor module being individually identifiable and controllable by the controller, the bioreactor modules each including a cell culture section and one or more functional modules coupled to the cell culture section, the bioreactor modules being configured to be mechanically coupled to each other so as to form a group of bioreactor modules connected via snap-fit configurations; and a common platform configured to be interfaced with each bioreactor module and providing portions for at least on-line imaging, environmental control, and/or data acquisition, the module's configuration to be mechanically coupled being such that each of the bioreactor modules can be detached individually from the group without disrupting the remaining modules and such that the group can be transferred as a single unit into an incubator, wherein each bioreactor modules includes a perfusion chamber configured to receive and hold a tissue construct, wherein each bioreactor module is configured to be attached at a bottom portion thereof to said common platform, and wherein each bioreactor module includes a transparent bottom portion to permit in situ imaging and/or viewing of the tissue constructs through the bioreactor module bottom portions during mechanical stretching of the tissue constructs while the bioreactor modules are attached to the common platform.

2. The system of claim 1, wherein each bioreactor module is configured as a cartridge having a perfusion chamber configured to receive and hold a tissue construct, a gas exchanger coupled to the perfusion chamber, a pump coupled to the gas exchanger and the perfusion chamber, and an interface adapted to be connected to the controller for identification, control and data exchange functions carried out between the cartridge and controller.

3. The system of claim 2, wherein the perfusion chamber includes a lid, a loading platen adapted to be connected to an external actuator so as to provide mechanical stimulation to the tissue construct, a PDMS gasket adapted to hold the tissue construct, a porous platen and a container.

4. The system of claim 2, wherein the perfusion chamber includes a lid, an alignment cover adapted to hold the tissue construct, one or more electrodes connected to electrode wiring, the electrodes adapted to provide electrical stimulation to the tissue construct, a PDMS gasket, one or more standoffs and a cartridge container.

5. The system of claim 2, wherein the perfusion chamber includes a cover, perfusion tubing, a transparent layer adapted to hold the tissue construct, a cartridge container, an indenter and an objective lens.

6. The system of claim 5, wherein the transparent layer and tissue construct are adapted to hold a tissue construct plane constant relative to the objective lens during mechanical stretching of the tissue construct so as to enable imaging of the tissue construct.

7. The system of claim 5, wherein the functional modules can include one or more of:

a pump module adapted to connect to the cell culture section and exchange medium with the cell culture section;

a motor module and a mechanical transmission module adapted to connect to the cell culture section and provide mechanical stimulus to the cell culture section;

an environmental control module adapted to connect to the cell culture module and regulate an environmental factor of the cell culture section; and a signal generation module adapted to connect to the cell culture section and to generate a stimulus signal to be applied to the cell culture module.

8. The system of claim 1, wherein each bioreactor module is independently provided with medium for perfusion into cells contained within the cell culture section.

9. The system of claim 1, wherein each bioreactor module includes universal connectors adapted to couple the bioreactor module to another corresponding universal connector on one of the functional modules.

10. The system of claim 1, including a microscope objective lens for imaging of the cell culture.

11. A modular bioreactor system comprising:

a top portion removably connected to a bottom portion to form a sealed unit, the sealed unit configured to include a plurality of bioreactor modules, each bioreactor module being individually identifiable and controllable by a controller, the bioreactor modules each including a cell culture section and one or more functional modules coupled to the cell culture section, the bioreactor modules being configured to be mechanically coupled so as to form a group of connected bioreactor modules, each bioreactor module being individually removable from the sealed unit; and a controller having a data processing device and a computer readable medium, the computer readable medium having stored thereon software instructions that, when executed by the data processing device, cause the data processing device to perform operations including controlling the bioreactor system and acquiring data from the bioreactor system, wherein each bioreactor module includes a perfusion chamber configured to receive and hold a tissue construct, a gas exchanger coupled to the perfusion chamber, a pump coupled to the gas exchanger and the perfusion chamber, and an interface adapted to be connected to the controller for identification, control and data exchange functions carried out between the cartridge and the controller, the perfusion chamber including a top plate, a loading platen adapted to be connected to an external actuator so as to provide mechanical stimulation to the tissue construct, a gasket adapted to hold the tissue construct, a container, a bottom plate, and a microscope objective, the bottom plate being configured to fit onto the microscope objective to enable imaging of the tissue construct during the mechanical stimulation of the tissue construct.

12. The system of claim 11, wherein the gasket and tissue construct are configured to hold a tissue construct plane constant relative to the microscope objective during mechanical stimulation of the tissue construct.

13. The system of claim 11, wherein each bioreactor module is configured as a cartridge including the perfusion chamber configured to receive and hold a tissue construct, a gas exchanger coupled to the perfusion chamber, a pump coupled to the gas exchanger and the perfusion chamber, and an interface adapted to be connected to the controller for identification, control and data exchange functions carried out between the cartridge and controller.

14. The system of claim 13, wherein the bioreactor cartridges are configured to be snap-fit together and placed as a unit into the sealed unit.

15. The system of claim 11, wherein the functional modules can include one or more of:
- a pump module adapted to connect to the cell culture section and exchange medium with the cell culture section;
- a motor module and a mechanical transmission module adapted to connect to the cell culture section and provide mechanical stimulus to the cell culture section;
- an environmental control module adapted to connect to the cell culture module and regulate an environmental factor of the cell culture section; and
- a signal generation module adapted to connect to the cell culture section and to generate a stimulus signal to be applied to the cell culture module.

16. The system of claim 11, wherein the transparent layer and tissue construct are adapted to hold a tissue construct plane constant relative to the objective lens during mechanical stretching of the tissue construct so as to enable imaging of the tissue construct, wherein the indenter is hollow and having the shape of a microscope objective, a movement of the construct over the indenter to maintain a same plane of view during an interval of imaging and mechanical motion.

17. The system of claim 1, wherein the common platform configured to be interfaced with each bioreactor module provides portions for at least on-line imaging.

18. The system of claim 17, wherein each bioreactor module includes a construct support portion configured for supporting a tissue construct, and the transparent bottom portions of the bioreactor modules are movable with respect to at least a portion of said construct support portion.

19. The system of claim 18, wherein said construct support portion of said each bioreactor module is configured such that said tissue construct is visible from below said each bioreactor module.

20. A modular bioreactor system comprising:
- a controller having a data processing device and a computer readable medium, the computer readable medium having stored thereon software instructions that, when executed by the data processing device, cause the data processing device to perform operations including controlling the bioreactor system and acquiring data from the bioreactor system;
- one or more bioreactor modules, each being individually identifiable and controllable by the controller, the bioreactor modules each including a cell culture section and one or more functional modules coupled to the cell culture section, the bioreactor modules being configured to be mechanically coupled to each other so as to form a group of bioreactor modules connected via snap-fit configurations,
- the module's configuration to be mechanically coupled being such that each of the bioreactor modules can be detached individually from the group without disrupting the remaining modules and such that the group can be transferred as a single unit into an incubator,
- wherein each bioreactor module is configured as a cartridge having a perfusion chamber configured to receive and hold a tissue construct,
- wherein the perfusion chamber includes a cover, perfusion tubing, a transparent layer adapted to hold the tissue construct, a cartridge container, an indenter and an objective lens positioned below the indenter,
- wherein the transparent layer and tissue construct are adapted to hold a tissue construct plane constant relative to the objective lens during mechanical stretching of the tissue construct, and
- wherein, during the mechanical stretching of the tissue construct, the bioreactor module allows viewing of the tissue construct from a bottom portion thereof through the objective lens.

* * * * *